US008147901B2

(12) United States Patent
Jung et al.

(10) Patent No.: US 8,147,901 B2
(45) Date of Patent: Apr. 3, 2012

(54) METHOD OF MANUFACTURING GAS SENSOR

(75) Inventors: Sung-ouk Jung, Yongin-si (KR);
Myung-sup Jung, Yongin-si (KR);
Soo-suk Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 622 days.

(21) Appl. No.: 11/742,639

(22) Filed: May 1, 2007

(65) Prior Publication Data
US 2008/0113301 A1  May 15, 2008

(30) Foreign Application Priority Data

Aug. 31, 2006  (KR) .................. 10-2006-0083658

(51) Int. Cl.
*B05D 5/12*  (2006.01)
(52) U.S. Cl. .......... 427/58; 977/890; 977/892; 977/900; 977/901
(58) Field of Classification Search .............. 427/58; 977/890, 892, 900, 901
See application file for complete search history.

(56) References Cited

U.S. PATENT DOCUMENTS

| 5,322,602 | A  | * | 6/1994 | Razaq ................... 205/788 |
| 5,605,612 | A  | * | 2/1997 | Park et al. .............. 204/429 |
| 6,137,107 | A  | * | 10/2000 | Hanson et al. .......... 250/332 |
| 6,335,793 | B1 | * | 1/2002 | Freeman et al. ......... 356/477 |
| 6,346,136 | B1 | * | 2/2002 | Chen et al. ............... 75/343 |
| 7,053,532 | B2 | * | 5/2006 | Lean et al. .............. 310/357 |
| 2003/0151344 | A1 | * | 8/2003 | Cheng et al. ........... 313/311 |
| 2004/0161867 | A1 | * | 8/2004 | Lee et al. ................ 438/20 |
| 2005/0032254 | A1 | * | 2/2005 | Cheng et al. ............ 438/20 |
| 2007/0212290 | A1 | * | 9/2007 | Zheng et al. ........... 423/445 B |

OTHER PUBLICATIONS

Liu, et al.; "Fullerine Pipes"; Science; vol. 280; pp. 1253-1256; May 22, 1998.
Rinzler, et al.; "Large-scale purification of single-well carbon nanotubes: process, product, and characterization"; Appl. Phys. A; vol. 67; pp. 29-37; 1998.
Lee, K., et al.; "Single Wall Carbon Nanotubes for p-Type Ohmic Contacts to GaN Light-Emitting Diodes"; Nano Letters; vol. 4, No. 5; pp. 911-914; 2004.
Sun, Z., et al.; "Decoration carbon nanotubes with Pd and Ru nanocrystals via inorganic reaction route in supercritical carbon dioxide-methanol solution"; Journal of Colloid and Interface Science; vol. 304; pp. 323-328; 2006.
Kumar, M.K., et al.; "Palladium dispersed multiwalled carbon nanotubes based hydrogen sensor for fuel cell applications"; International Journal of Hydrogen Energy; vol. 32; pp. 2518-2536; 2007.
Lu, Y., et al.; "A carbon nanotube sensor array for sensitive gas discrimination using principal component analysis"; Journal of Electroanalytical Chemistry; vol. 593; pp. 105-110; 2006.
Sayago, I., et al.; "Novel selective sensors based on carbon nanotube films for hydrogen detection"; Sensors and Actuators B; vol. 122; pp. 75-80; 2007.
European Search Report dated Jan. 18, 2008 for Application No. 07104027.3.

* cited by examiner

*Primary Examiner* — Shamim Ahmed
(74) *Attorney, Agent, or Firm* — Cantor Colburn LLP (57) ABSTRACT

Provided herein is a method of manufacturing a gas sensor. The method includes forming electrodes on a surface of a substrate, manufacturing a paste having a complex of CNTs and a metal-ligand complex comprising a metal that has gas adsorption selectivity for specific gases, coating the paste on the substrate to cover the electrodes, patterning the paste by a photolithography process, and reducing the metal-ligand complex included in the patterned paste.

13 Claims, 5 Drawing Sheets

METHOD OF MANUFACTURING GAS SENSOR

This application claims priority to Korean Patent Application No. 10-2006-0083658, filed on Aug. 31, 2006, and all the benefits accruing therefrom under 35 U.S.C. §119, the content of which is incorporated herein by reference in its entirety.

BACKGROUND OF THE INVENTION

1. Field of the Invention

The present invention relates to a method of manufacturing a gas sensor, and more particularly, to a simple method of manufacturing a gas sensor having an improved sensitivity and adsorption selectivity with respect to a specific gas.

2. Description of the Related Art

While it is true that scientific developments have improved the quality of human life, the extensive and rapid destruction of nature caused by industrialization and environmental contamination due to increased energy consumption pose a great threat to human beings.

Accordingly, the development of a reliable and highly sensitive gas sensor that can detect and quantify different kinds of harmful gases that can cause air contamination is needed. Presently, gas sensors are widely used in various industries (such as the manufacturing industry, the agricultural industry, the livestock industry, the office equipment industry, the catering industry, and the ventilation industry), crime prevention (alcohol level checking), environment (air contamination surveillance, combustion control), disaster prevention (gas leaking, oxygen deficiency alarm in mines, fire surveillance), medical (gas analysis in blood, anesthesia gas analysis), and the like, and further applications for gas sensors are widening every day.

In general operation, a gas sensor measures the amount of a harmful gas by using the characteristics of changes in electrical conductivity or electrical resistance according to the degree of adsorption of gas molecules. Gas sensors have been manufactured using a metal oxide semiconductor, a solid electrolyte material, or other organic materials. However, gas sensors that use a metal oxide semiconductor or a solid electrolyte material start the sensing operation when the gas sensor is heated to 200-600° C. Gas sensors that use an organic material have a very low electrical conductivity, and specifically gas sensors that use carbon black and an organic complex have a very low sensitivity.

Carbon nanotubes ("CNTs") have recently drawn attention as new materials that can be applied to various industrial fields due to their high electron emission characteristics and high chemical reactivity. A particular attribute of CNTs is that CNTs are materials that have very large surface areas relative to the volume of the CNTs. Therefore, the CNT is very useful in fields such as the detection of minute amounts of chemical components and for hydrogen storage. A gas sensor that uses CNTs detects harmful gases by measuring the electrical signal (for example, conductance or resistance) that changes according to the electronic property of a gas adsorbed to the CNTs. CNTs, when used in a gas sensor, are advantageous in that sensing operations of the gas sensor can start at room temperature, and sensitivity and speed of response are very high since there is high electrical conductivity in the CNTs when harmful gases such as $NH_3$ or $NO_2$ react with CNTs in the gas sensor.

However, a gas sensor that only uses CNTs has poor selectivity with respect to a specific gas. As a method of supplementing the drawback of a gas sensor that only uses CNTs, a metal that has adsorption selectivity with respect to a specific gas can be deposited on CNTs using a sputtering method or a chemical vapor deposition ("CVD") method. However, this method requires expensive equipment such as a sputtering apparatus or a CVD apparatus, and the manufacturing process of such a gas sensor is also very complicated.

BRIEF SUMMARY OF THE INVENTION

Disclosed herein is a method of simply manufacturing a gas sensor having an improved sensitivity and adsorption selectivity with respect to a specific gas.

In an embodiment, a method of manufacturing a gas sensor, comprises: forming electrodes on a surface of a substrate; manufacturing a paste having a complex of CNTs and a metal-ligand complex of a metal that has gas adsorption selectivity for specific gases; coating the paste on the surface of the substrate to cover the electrodes; patterning the paste using a photolithography process; and reducing the metal-ligand complex included in the patterned paste.

In another embodiment, in the manufacturing of the paste, the CNTs are modified CNTs having functional groups that can generate cross-links by exposure to light.

In another embodiment, the modified CNTs can be manufactured by substituting (meth)acrylate functional groups for carboxylic acids present on surfaces of the CNTs.

In another embodiment, the paste can further comprise trimethoxysilyl methacrylate In another embodiment, in the manufacturing of the paste, the paste can comprise a photoresist. The photoresist can be a negative photoresist in which a non-exposed portion is removed by a developing agent or a positive photoresist in which an exposed portion is removed by a developing agent.

In an embodiment, the paste can be patterned to uncover the electrodes.

In another embodiment, the metal-ligand complex can be reduced by heat and a reducing agent. In this case, the reduction of the metal-ligand complex is performed by baking the patterned paste under a $H_2$ and $N_2$ atmosphere.

In another embodiment, a method of manufacturing a gas sensor, comprises forming electrodes on a surface of a substrate; manufacturing a paste consisting essentially of modified CNTs comprising radical cross-linking functional groups, a photo-initiator, and a metal-ligand complex comprising a metal that has adsorption selectivity with respect to specific gases, or CNTs comprising carboxylic acid functional groups, a photoresist, and a metal-ligand complex comprising a metal that has gas adsorption selectivity for specific gases; coating the paste on the surface of the substrate to cover the electrodes; patterning the paste by a photolithography process; and reducing the metal-ligand complex included in the patterned paste.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings in which exemplary embodiments of the invention are shown.

It will be understood that when an element is referred to as being "on" another element, it can be directly on the other element or intervening elements may be present therebetween. In contrast, when an element is referred to as being "disposed on" or "formed on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements and the thicknesses of layers and regions are exaggerated for clarity.

FIGS. 1A, 1B, 2A, 2B, 3A, 3B, 4A, and 4B are drawings for explaining a method of manufacturing a gas sensor according to an embodiment of the present invention.

Figure 1A:
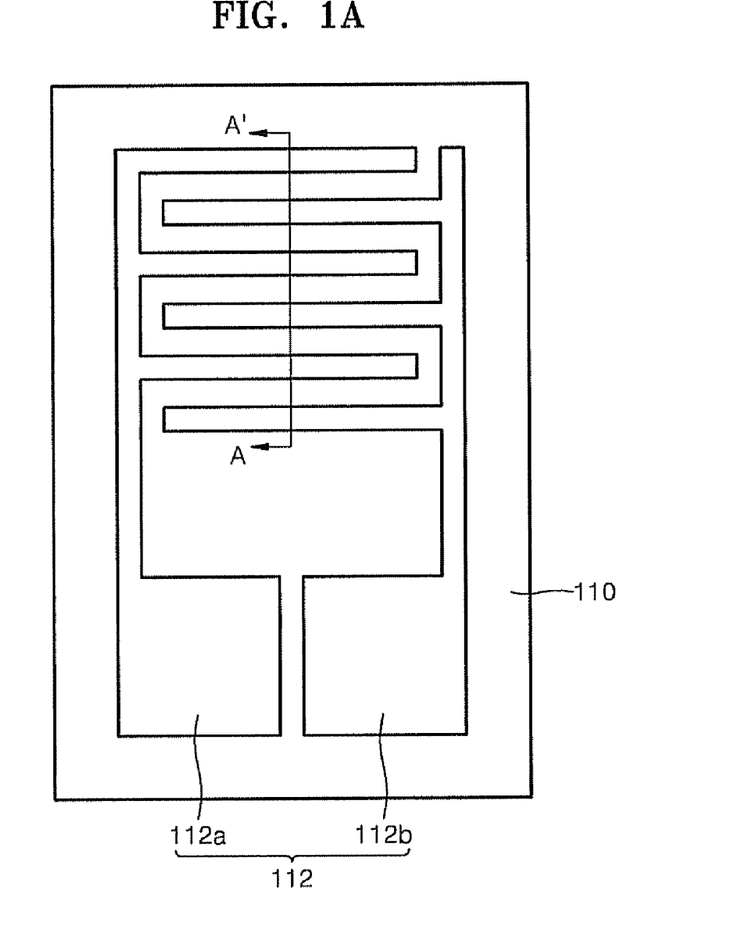
FIGS. 1A, 1B, 2A, 2B, 3A, 3B, 4A, and 4B are drawings explaining an exemplary method of manufacturing a gas sensor according to an embodiment of the present invention.
Figure 1B:
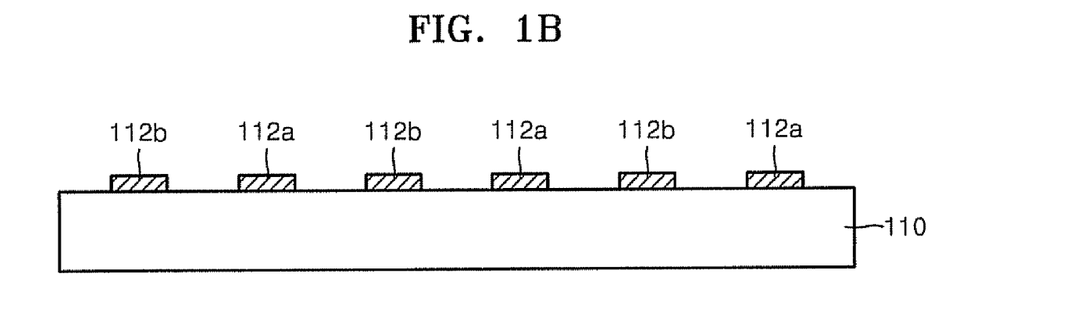

FIG. 1A is a plan view illustrating electrodes formed on a surface of a substrate 110 and FIG. 1B is a cross-sectional view taken along the line A-A' of FIG. 1A.

Referring to FIGS. 1A and 1B, electrodes 112 including a first electrode 112a and a second electrode 112b are formed on a surface of substrate 110. The first and second electrodes 112a and 112b can be formed in, for example, an interdigitated shape, but the shape of the first and second electrodes 112a and 112b is not limited thereto and the electrodes can be formed in various other shapes. The first and second electrodes 112a and 112b can be formed by patterning a metal material having a favorable electrical conductivity after the material is deposited on the substrate 110. The first and second electrodes 112a and 112b can be formed of, for example, Au or Ti, but is not limited thereto.

Figure 2A:
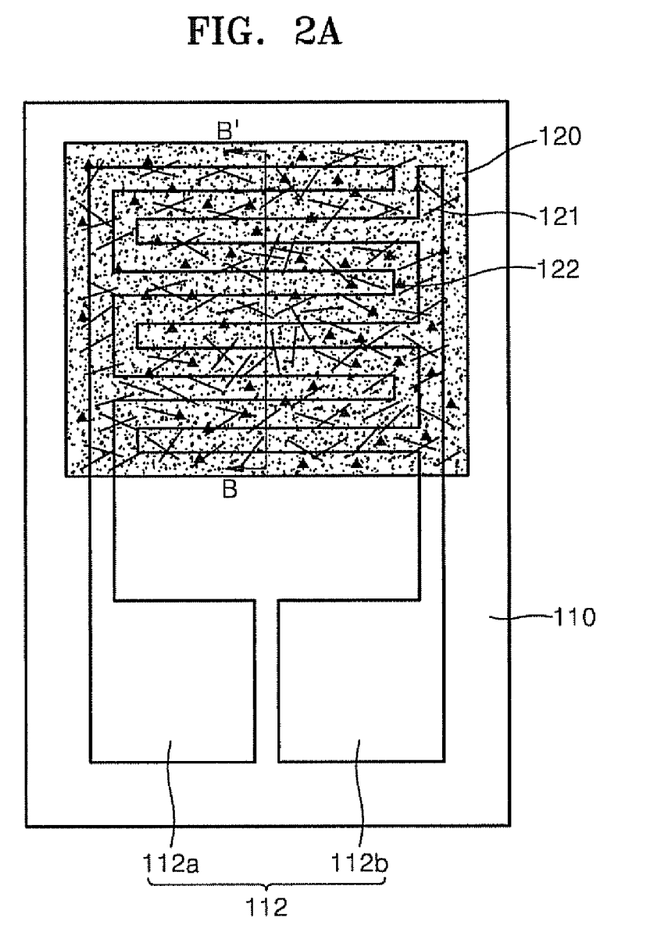
Figure 2B:
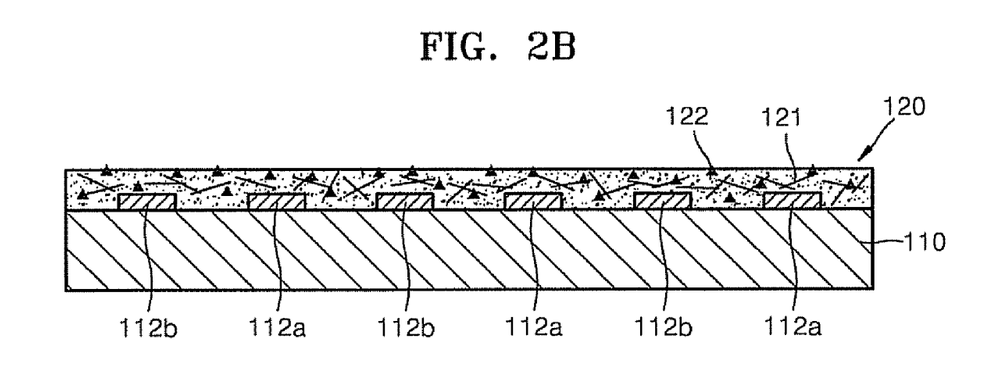

FIG. 2A is a plan view illustrating the coating of a paste 120 on a surface of the substrate 110 on which the electrodes 112 are formed, and FIG. 2B is a cross-sectional view taken along the line B-B' of FIG. 2A.

Referring to FIGS. 2A and 2B, the paste 120, which is a mixture comprising modified CNTs 121 and a metal-ligand complex 122, is prepared. The paste 120 can be manufactured by uniformly distributing the metal-ligand complex 122 and the modified CNTs 121 in a solvent. In this case, the paste 120 can further include a surfactant and a photo-initiator.

In the current embodiment, modified CNTs 121 having functional groups, such as a (meth)acrylate that can cause cross-linking by exposure to light are used. The modified CNTs 121 can be manufactured by substituting radical cross-linking functional groups, such as for example (meth)acrylate functional groups for the carboxylic acid functional groups present on surfaces of the CNTs. More specifically, the modification of the CNTs can be performed by the reaction according to Scheme (1).

Scheme (1)

Referring to the above reaction, the carboxylic acid present on the surfaces of the CNTs can be modified with (meth)acrylates including acrylates and methacrylates by reacting with (meth)acrylate monomers (e.g., acryloyl chloride, or methacryloyl chloride as shown in Scheme 1) in the presence of, for example, a base such as $(C_2H_5)_3N$ and a solvent such as dimethylformamide ("DMF"), to form the mixed anhydride. The base and (meth)acryloyl chloride are used in about a 1:1 molar ratio, and are in a molar excess relative to the number of moles of carboxylic acid functional groups present on the CNT The carboxylic acid modified SWCNT can be prepared by the chemical oxidation of purified single-wall nanotubes ("SWCNTs") in an acidic mixture as reported previously (J. Liu, A. G. Rinzler, H. Dai, J. H. Hafner, R. K. Bradley, P. J. Boul, A. Lu, T. Iverson, K. Shelimov, C. B. Huffman, F. Rodriguez-Marcfas, Y. -S. Shon, T. R. Lee, D. T. Colbert, R. E. Smalley, *Science* 1998, vol. 280, p. 1253; G. Rinzler, J. Liu, H. Dai, P. Nikolaev, C. B. Huffman, F. Rodriguez-Marcfas, P. J. Boul, A. H. Lu, D. Heymann, D. T. Colbert, R. S. Lee, J. E. Fischer, A. M. Rao, P. C. Eklund, R. E. Smalley, *Appl. Phys. A* 1998, vol. 67, p. 29.).

The (meth)acrylates present on the surfaces of the modified CNTs 121 are cross-linked to each other by the action of a photo-initiator during exposure. Here, the photo-initiator initiates the cross-linking reaction of the (meth)acrylate groups by absorbing energy from ultraviolet light rays used to expose the CNT complex, thereby generating free radicals which react with the (meth)acrylates to thereby induce free radical coupling between (meth)acrylates on adjacent CNTs. In a specific embodiment, the paste consists essentially of modified CNTs, a photo-initiator, and a metal-ligand complex. Meanwhile, the paste 120 can further include a material, such as for example trimethoxysilyl methacrylate, 3-trimethoxysilylpropyl methacrylate, or 3-trimethoxysilyipropyl acrylate, but not limited to these, for improving the cross-linking characteristics between the modified CNTs 121 and the substrate 110.

Also, in the current embodiment, a metal-ligand complex 122 that includes a metal having adsorption selectivity for a specific gas or gases is used. Certain gases can be adsorbed by specific metals. Specifically, in an embodiment, a gas selected from the group consisting of dichloroethylene, acetic acid, and propanoic acid can be adsorbed to Ag, and a gas selected from the group consisting of ethylene, benzene, and cyclohexane can be adsorbed to Ir. Also, a gas selected from the group consisting of methane and formic acid can be adsorbed to Mo, and a gas selected from the group consisting of methane, methanol, and benzene can be adsorbed to Ni. A gas selected from the group consisting of benzene, acetylene, ethylene, methanol, benzene+CO, and methane can be adsorbed to Pd, and a gas selected from the group consisting of aniline, ammonia, cyanobenzene, m-xylene, naphthalene, N-butylbenzene, and acetonitrile can be adsorbed to Pt. In addition, there are various uncomplexed metals that have an adsorption selectivity for specific gases that may be included. In an embodiment, a gas sensor is manufactured using a metal that selectively adsorb specific gases. That is, a metal that has adsorption selectivity with respect to specific gases as described above is included in the metal-ligand complex 122 that is mixed with the modified CNTs 121.

Next, the paste 120 manufactured as above is coated on the surface of the substrate 110 on which the electrodes 112 are formed. Here, the paste 120 can be coated on the surface of substrate 110 to cover the electrodes 112. The paste 120 can be coated on the surface of the substrate 110 by, for example, spin coating or spray coating. The method of coating of the paste 120 is not limited to the above methods, but can be coated by other methods.

Figure 3A:
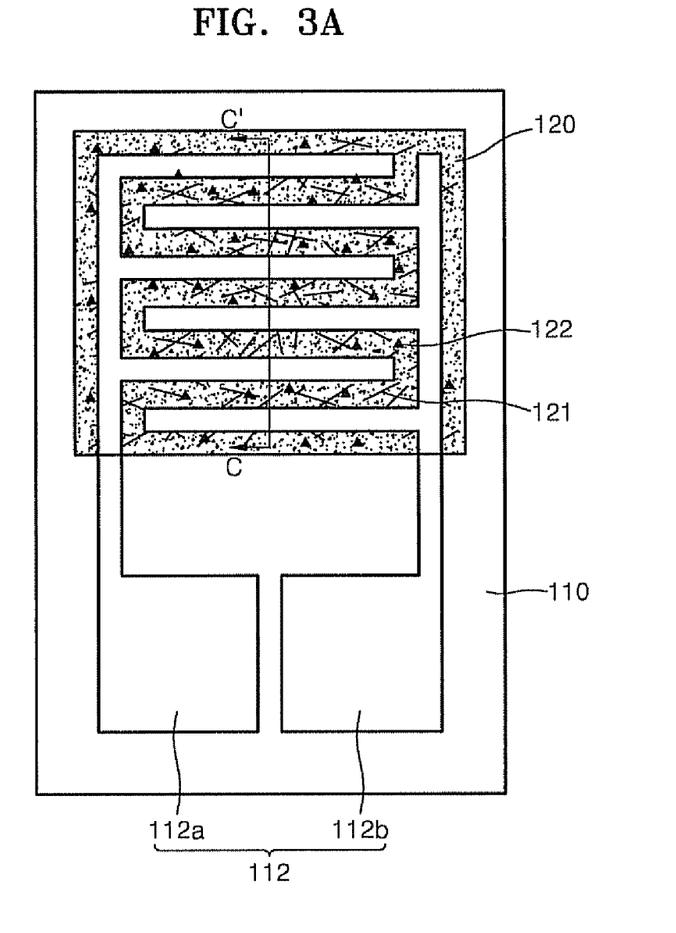
Figure 3B:
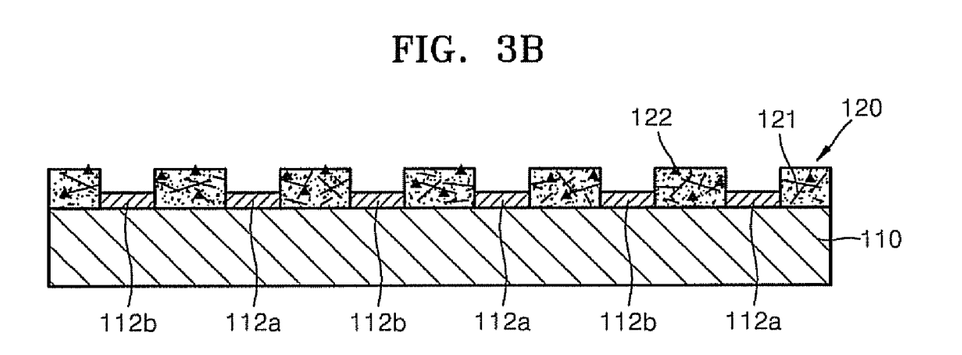

FIG. 3A is a plan view illustrating a patterned paste 120 coated on a surface of substrate 110, and FIG. 3B is a cross-sectional view taken along the line C-C' of FIG. 3A.

Referring to FIGS. 3A and 3B, volatile materials contained in the paste 120 coated on the surface of substrate 110 are removed through a prebake process. The paste 120 coated on the substrate 110 is patterned into a predetermined shape by photolithography. Here, the paste 120 can be patterned to uncover the electrodes 112 (shown in FIG. 3A). As a result of the patterning, the paste 120 only remains between first electrode 112a and second electrode 112b (shown in FIG. 3B). More specifically, a photomask (not shown) having a predetermined pattern is provided above the substrate 110 on which the paste 120 is coated. Afterwards, the paste 120 is exposed through the photomask. The (meth)acrylates of the modified CNTs 121 are cross-linked to each other in exposed portions of the paste 120 (where the paste comprises a negative-tone photoresist). Next, un-exposed paste 120 is removed using a developing agent. When the paste 120 coated on the substrate 110 to cover the electrodes 112 is patterned, the gas adsorption area is greatly enlarged, thereby increasing the sensitivity of the gas sensor.

Figure 4A:
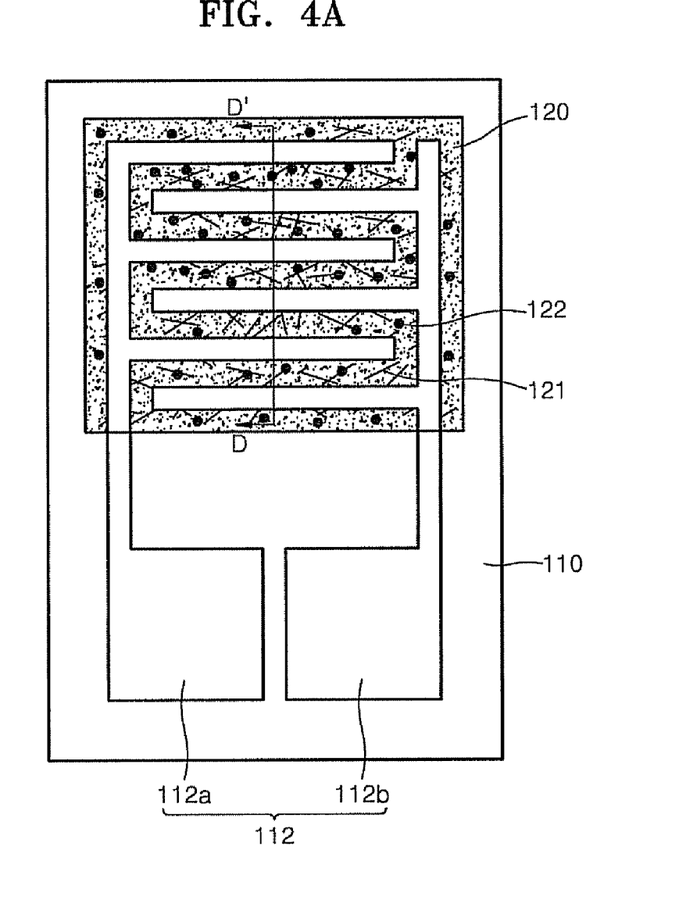
Figure 4B:
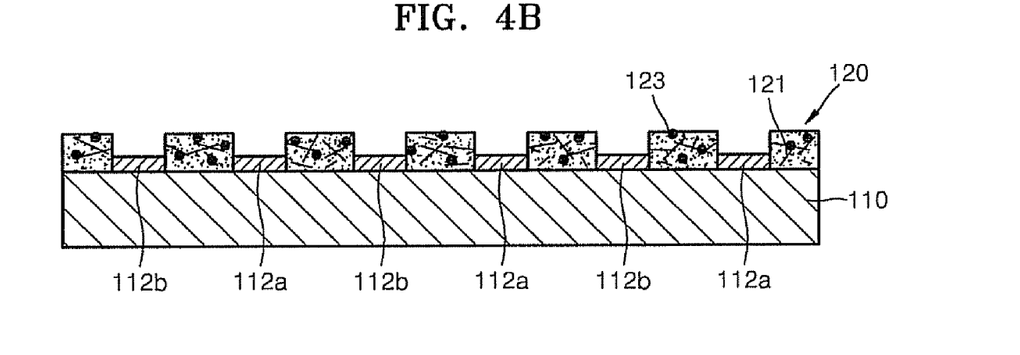

FIG. 4A is a plan view illustrating a state in which the metal-ligand complex 122 in the patterned paste 120 is reduced, and FIG. 4B is a cross-sectional view taken along the line D-D' of FIG. 4A.

Referring to FIGS. 4A and 4B, when the metal-ligand complex 122 in the patterned paste 120 is reduced to a metal 123, the manufacture of a gas sensor according to an embodiment of the present invention is complete. The reduction of the metal-ligand complex 122 can be performed using heat and a reducing agent. More specifically, for example, the metal-ligand complex 122 can be reduced by baking the paste 120 at a predetermined temperature under a $H_2$ and $N_2$ atmosphere. In this way, when the metal-ligand complex 122 is reduced, a complex of modified CNTs 121 and a metal 123 that has adsorption selectivity with respect to specific gases is present in the paste 120.

Experimental Embodiment 1: Manufacture of a Gas Sensor

A dispersion of $PdCl_2$ (0.006 g/ml) was used as a metal-ligand complex having a metal, for example, Pd that has adsorption selectivity with respect to specific gases. A dispersion of carboxylic acid-modified single-walled carbon nanotubes (SWCNTs, 0.012 g/ml) were used.

The $PdCl_2$ and the modified SWCNTs were mixed in a mixing ratio of 1:1 v/v in a N,N-dimethylformamide ("DMF") solvent by sonication.

The manufactured paste was coated by spin coating on a surface of a substrate (such as, for example, silicon, quartz, or the like) on which electrodes are formed. Next, the paste coated on the substrate was patterned by exposure and development.

The patterned paste was baked for approximately 4 hours at a temperature of approximately 250° C. under a $H_2$ and $N_2$ atmosphere. Through the above process, a complex of Pd and modified CNTs was formed by reducing the $PdCl_2$, which is the metal-ligand complex, in the paste.

Experimental Embodiment 2: Gas Measurement

Variation in conductance, $\Delta G=[G(\text{hydrogen})-G(\text{air})]/G(\text{air})$ (where G represents conductance in different atmospheres, here, hydrogen or air), of gas sensors for detecting changes in concentration of hydrogen gas, which selectively reacts with Pd, was measured using the gas sensor that includes the complex of Pd and modified CNTs and was manufactured according to experimental embodiment 1, and a gas sensor that only includes modified CNTs. The concentrations of the hydrogen gas used were 250 ppm, 500 ppm, 1,250 ppm, and 2,500 ppm, and the conductance variations were measured at room temperature.

Figure 5:
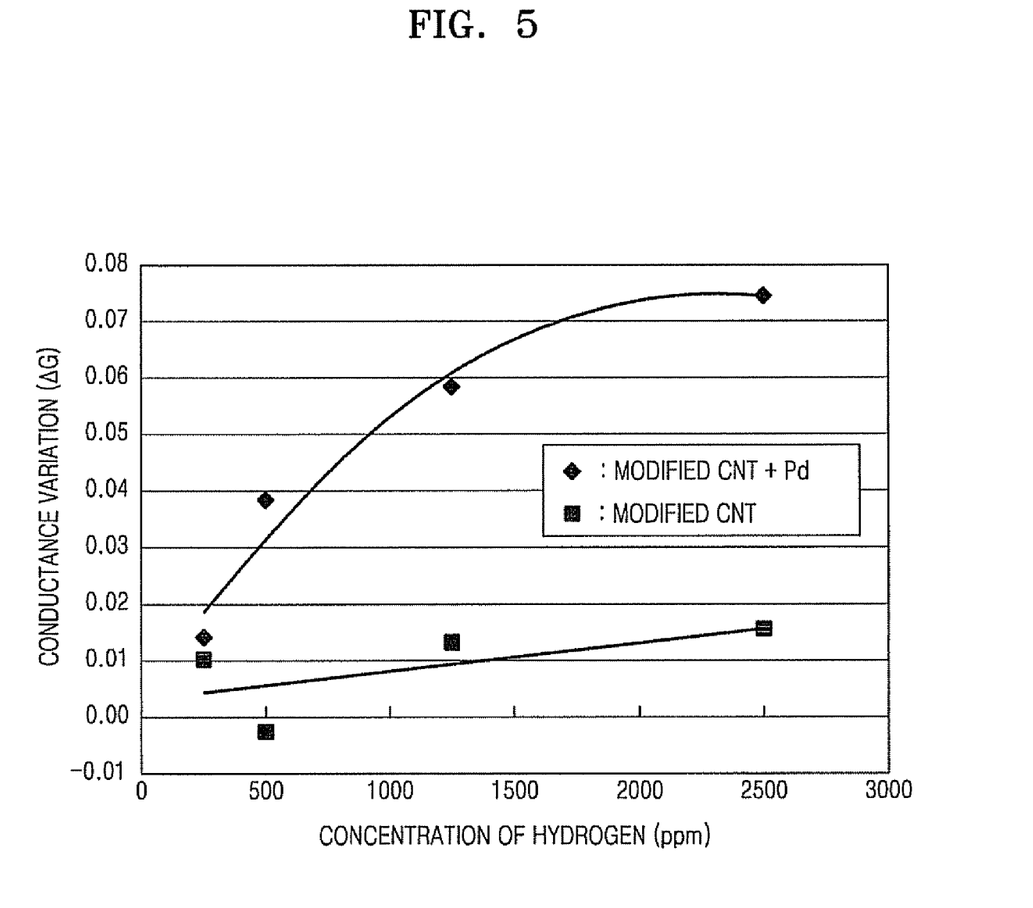
FIG. 5 is a graph showing a comparison of conductance variations with respect to the concentration of hydrogen gas in a comparative gas sensor that only uses modified CNTs and in an exemplary gas sensor that uses a complex of modified CNTs and Pd, according to an embodiment of the preset invention.

Measurement results are shown in FIG. 5. FIG. 5 is a graph showing the comparison of conductance variations with respect to the concentration of hydrogen gas in a gas sensor that only uses modified CNTs and a gas sensor that uses a complex of modified CNTs and Pd, according to an embodiment of the preset invention. Referring to FIG. 5, as the concentration of hydrogen gas was increased to 250 ppm, 500 ppm, 1,250 ppm, and 2,500 ppm, the conductance variations of the gas sensor that only uses the modified CNTs were 0.01, 0.00, 0.01, and 0.01, respectively, and the conductance variations of the gas sensor that uses the complex of Pd and modified CNTs were 0.01, 0.04, 0.06, and 0.07, respectively. That is, the gas sensor that only uses the modified CNTs has almost no conductance variation corresponding to the increase in the concentration of hydrogen gas. However, in the gas sensor that uses the complex of Pd and modified CNTs according to the present embodiment, the conductance variation increases with respect to increases in the concentration of hydrogen gas. From the result of the experiment, it is seen that the gas sensor that uses only modified CNTs does not have selectivity for hydrogen gas, but the gas sensor that uses a complex of Pd and modified CNTs has selectivity for hydrogen gas.

As described above, the gas sensor manufactured according to the an embodiment of the present invention has gas adsorption selectivity for specific gases, unlike the gas sensor that only uses modified CNTs by using a complex of modified CNTs and a metal that has adsorption selectivity with respect to specific gases. Also, since the complex of modified CNTs and metal is selectively formed between electrodes by patterning the paste, the area for gas adsorption is increased, thereby further increasing the sensitivity of the gas sensor.

Also, in the current embodiment, since the modified CNTs themselves, which have functional groups that can cause a cross-linking reaction by exposure, are used as a cross-linking agent, a high temperature baking process required when a polymer cross-link agent is used is unnecessary. Also, in manufacturing a paste, residual impurities remaining in the sensing film of the gas sensor can be reduced by minimizing the use of impurities in the paste.

In the above (first) embodiment, the manufacture of a gas sensor using modified CNTs has been described. However, a gas sensor can also be manufactured using non-modified CNTs as described below.

A method of manufacturing a gas sensor according to another (second) embodiment will now be described. Drawings for describing the method of manufacturing a gas sensor are similar to drawings 1A through 4B, and thus, a further description of the drawings will not be repeated.

In the second embodiment, a paste is manufactured by uniformly dispersing non-modified CNTs (0.006 g/ml of e.g., carboxylic acid modified carbon nanotubes, a metal-ligand complex (0.012 g/ml) that has adsorption selectivity for a specific gas or gases, and a photoresist. Here, the metal-ligand complex is also as described in detail in the first embodiment, thus, a description thereof will not be repeated. In a specific embodiment, the paste consists essentially of CNTs having carboxylic acid groups, a photoresist, and a metal-ligand complex. The photoresist can be a negative photoresist, a non-exposed portion of which is removed by a developing agent, or a positive photoresist, and an exposed portion of which is removed by a developing agent (such as, for example, 0.26N TMAH developer).

After the paste manufactured as above is coated to cover the electrodes on a substrate, the paste is patterned into a predetermined shape by exposing and developing the paste using a photolithography process such as, for example, g-Line, i-Line, DUV, 193 nm, e-beam, x-ray, EUV, or other photolithographic process. The paste can thus be patterned and developed to uncover (i.e., remove the paste overlying) the electrodes.

Afterwards, the metal-ligand complex included in the paste is reduced to a metal using heat and a reducing agent (such as, for example, forming gas). Thus, the manufacture of a gas sensor according to this embodiment is completed by reducing the metal-ligand complex by baking the paste at a predetermined temperature under a $H_2$ and $N_2$ atmosphere.

As described above, a gas sensor prepared according to the method of the present invention provides the following advantages.

Firstly, since a gas sensor is manufactured using a paste made by mixing a metal-ligand complex and modified CNTs (or metal-ligand complex, unmodified CNT, and photoresist), the gas sensor can be manufactured by a much simpler process when compared to a conventional process in which sputtering or chemical vapor deposition is used.

Secondly, since the gas sensor manufactured according to the present invention includes not only CNTs but also a metal that has adsorption selectivity for specific gases, the gas sensor can thereby have adsorption selectivity for specific gases unlike a conventional gas sensor that is manufactured only using CNTs.

Thirdly, since a complex of Pd and CNTs is only formed between electrodes due to the patterning of the paste, the gas adsorption area increases, thereby further increasing sensitivity of the gas sensor.

Fourthly, when modified CNTs having functional groups that can cause cross-link reaction by exposure are used, high temperature baking is unnecessary. Also, in manufacturing a paste, the residual impurities remaining in the sensing film of a gas sensor can be minimized by accordingly minimizing the presence of impurities in the paste.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of manufacturing a gas sensor, comprising:
    forming electrodes on a surface of a substrate; wherein the electrodes comprise first and second electrodes formed in an inter-digitated shape;
    manufacturing a paste comprising CNTs having functional groups that can generate cross-linking by exposure to light and a metal-ligand complex comprising a metal that has gas adsorption selectivity for specific gases; wherein the CNTs are manufactured by modifying carboxylic acid groups present on surfaces of the CNTs with (meth)acrylate groups;
    coating the paste on the surface of the substrate to cover the electrodes;
    patterning the paste by a photolithography process; and
    reducing the metal-ligand complex included in the patterned paste.

2. The method of claim 1, wherein the paste further comprises trimethoxysilyl methacrylate.

3. The method of claim 1, wherein, in the manufacturing of the paste, the paste further comprises photoresist.

4. The method of claim 3, wherein the photoresist is a negative photoresist in which a non-exposed portion is removed by a developing agent.

5. The method of claim 3, wherein the photoresist is a positive photoresist in which an exposed portion is removed by a developing agent.

6. The method of claim 1, wherein the paste is coated on the substrate by spin coating or spray coating.

7. The method of claim 1, wherein the paste is patterned to uncover the electrodes.

8. The method of claim 1, wherein the metal-ligand complex is reduced by heat and a reducing agent.

9. The method of claim 1, wherein the reduction of the metal-ligand complex is performed by baking the patterned paste under a $H_2$ and $N_2$ atmosphere.

10. A method of manufacturing a gas sensor, comprising:
    forming electrodes on a surface of a substrate; wherein the electrodes comprise first and second electrodes formed in an inter-digitated shape;
    manufacturing a paste consisting essentially of
        modified CNTs comprising radical cross-linking functional groups, a photo-initiator, and a metal-ligand complex comprising a metal that has gas adsorption selectivity for specific gases, or CNTs comprising carboxylic acid functional groups, a photoresist, and a metal-ligand complex comprising a metal that has adsorption selectivity with respect to specific gases; wherein the CNTs are manufactured by modifying carboxylic acid groups present on surfaces of the CNTs with (meth) acrylate groups;

coating the paste on the surface of the substrate to cover the electrodes;

patterning the paste by a photolithography process; and reducing the metal-ligand complex included in the patterned paste.

11. The method of claim 10, wherein the modified CNTs comprise (meth)acrylate functional groups.

12. The method of claim 10, wherein the photoresist is a negative photoresist or a positive photoresist.

13. A method of manufacturing a gas sensor, comprising:

forming electrodes on a surface of a substrate; wherein the electrodes comprise first and second electrodes formed in an inter-digitated shape;

manufacturing a paste consisting essentially of CNTs, a photoresist, and a metal-ligand complex comprising a metal that has gas adsorption selectivity for specific gases; wherein the CNTs are manufactured by modifying carboxylic acid groups present on surfaces of the CNTs with (meth)acrylate groups;

coating the paste on the surface of the substrate to cover the electrodes;

patterning the paste by a photolithography process; and reducing the metal-ligand complex included in the patterned paste.

* * * * *